US006858146B1

(12) United States Patent
Myers et al.

(10) Patent No.: US 6,858,146 B1
(45) Date of Patent: Feb. 22, 2005

(54) ARTIFICIAL LIVER APPARATUS AND METHOD

(75) Inventors: Edward F. Myers, Baltimore, MD (US); Albert P. Li, Bonita, CA (US); Achilles A. Demetriou, Los Angeles, CA (US)

(73) Assignee: Xenogenics, Warwick, RI (US)

( * ) Notice: Subject to any disclaimer, the term of this patent is extended or adjusted under 35 U.S.C. 154(b) by 0 days.

(21) Appl. No.: 08/809,677

(22) PCT Filed: Sep. 27, 1994

(86) PCT No.: PCT/US94/10935

§ 371 (c)(1),
(2), (4) Date: Feb. 20, 2002

(87) PCT Pub. No.: WO96/09876

PCT Pub. Date: Apr. 4, 1996

(Under 37 CFR 1.47)

Related U.S. Application Data

(63) Continuation-in-part of application No. 07/943,777, filed on Sep. 11, 1992, now abandoned.

(51) Int. Cl.[7] .................. B01D 61/00; B01D 63/02; C12N 5/08
(52) U.S. Cl. .............. 210/644; 210/195.2; 210/222; 210/252; 210/258; 210/321.6; 210/321.72; 210/321.78; 210/321.87; 210/500.23; 210/645; 210/649; 422/44; 422/48; 435/2; 435/325; 435/370; 435/395; 435/396; 435/402; 435/403; 436/177; 436/178
(58) Field of Search ......................... 210/195.2, 222, 210/252, 258, 321.6, 321.65, 321.72, 321.78, 321.87, 500.23, 644, 645, 649, 650, 767, 806, 929; 422/44, 45, 48, 101; 435/2, 1.2, 325, 353, 370, 395, 396, 402, 403, FOR 100–109, 284.1, 1.1; 436/177, 178

(56) References Cited

U.S. PATENT DOCUMENTS

| | | | | |
|---|---|---|---|---|
| 4,335,994 A | * | 6/1982 | Gurth .......................... | 415/90 |
| 4,853,324 A | * | 8/1989 | Viles et al. .................... | 435/2 |
| 4,963,490 A | * | 10/1990 | Churchouse et al. ........ | 435/401 |
| 5,011,607 A | * | 4/1991 | Shinzato ..................... | 210/637 |
| 5,043,260 A | * | 8/1991 | Jauregui ..................... | 435/1.1 |

OTHER PUBLICATIONS

Transactions of the American Society of Artificial Internal Organs, vol. XXI, issued 1975, C.F.W. Wolf et al, "Bilirubin Conjugation by An Artificial Liver Composed of Cultured Cells and Synthetic Capillaries", pp. 16–27.*

Journal of Surgical Research, vol. 48, No. 4 issued Apr. 1990, W.S. Arnaout et al., "Development of Bioartificial Liver: Bilirubin Conjugation in Gunn Rats", pp. 379–382.*

Olumide et al, Hepatic support with hepatocyte suspensions in a permeable membrane dialyzer, Surgery, Nov. 1977.*

* cited by examiner

Primary Examiner—John Kim
(74) Attorney, Agent, or Firm—Colleen McKiernan

(57) ABSTRACT

Artificial liver devices and methods for using the devices to purify a biological fluid are disclosed. The methods include the use of living hepatocytes (23) which are either unattached or attached to inert carriers and suspended in a cell culture medium which circulates in the devices with the hepatocytes (23). Blood or plasma passes on one side (7″) of semi-permeable membranes, on the other side (7) of which is the cell culture medium and across which is a concentration and/or pressure gradient. Solutes diffusing across the membrane into the cell culture medium are metabolized by the hepatocytes (23) and/or captured by additional removal means (4). Those undesirable substances which do not diffuse out of the blood or plasma into the hepatocyte containing culture medium are captured by additional removal means (50).

41 Claims, 2 Drawing Sheets

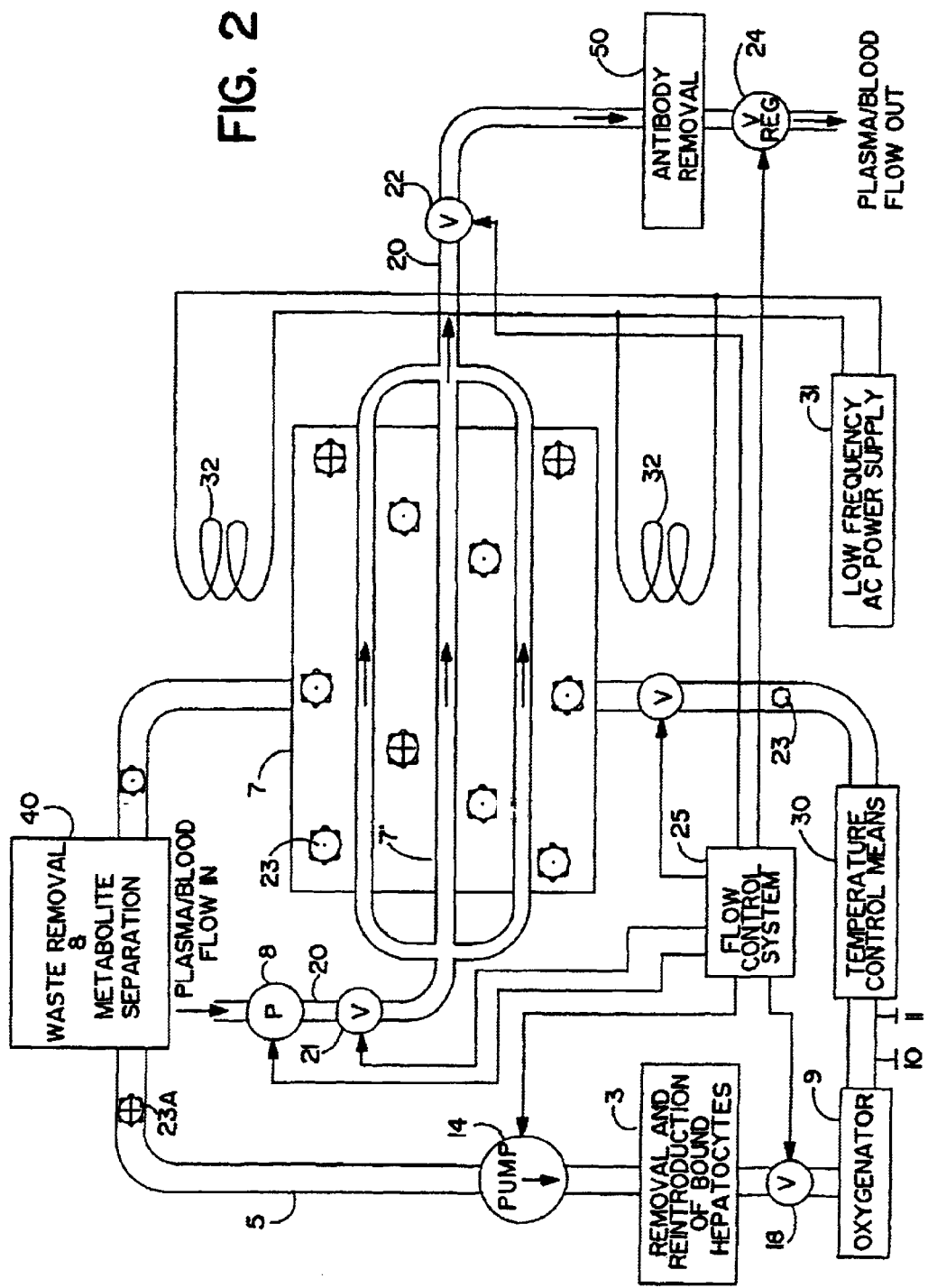

ARTIFICIAL LIVER APPARATUS AND METHOD

This application is a 371 of PCT/US94/10935 filed Sep. 27, 1994, which is a continuation-in-part of U.S. patent application Ser. No. 07/943,777, filed Sep. 11, 1992, now abandoned.

BACKGROUND OF THE INVENTION

1. Field of the Invention

This invention relates to an device and a process for the extracorporeal purification of blood and plasma. Specifically, it relates to a purification device which, while similar in structure to hemodialysis devices used in the treatment of renal insufficiencies, uses novel biological means to perform many of the functions of a normal human liver. The device and method are therefore intended to assist in the treatment and support of patients suffering from liver disease or who have undergone transplantation of liver tissue.

2. History of the Prior Art

To best understand the invention, an overview of principles of anatomy and physiology relating to human liver function and disease is useful. The liver is an organ divided into two principal lobes made up of functional units called lobules. A lobule consists of cords of hepatic cells arranged radially around a central vein. Between these cords are sinusoid spaces lined with phagocytic cells known as Kupffer cells. Oxygenated blood is provided to the liver via the hepatic artery while deoxygenated blood leaves the liver via the hepatic portal vein. Branches of these vessels deliver blood to the sinusoids, where oxygen, most nutrients and certain toxins are extracted into the hepatic cells.

More specifically, as glucose-rich blood passes through the liver, excess glucose is removed and stored as the polysaccharide glycogen. When the level of glucose in the blood drops below normal, glycogen will be broken down into glucose which is released by the hepatic cells into the blood stream. The liver also assists protein metabolism by extracting and storing excess amino acids in the bloodstream for use in the construction of many plasma proteins, such as albumin. Bile, a solution of salts, bilirubin, cholesterol and fatty acids which assists in the emulsification of fats and intestinal absorption of lipids, is also produced by hepatic cells. It is not, however, normally secreted into the bloodstream buy these cells but is instead transported to, and stored in, the gallbladder.

Of greater importance to this invention is not the liver's role in digestion of food but its role in regulating the concentration of wastes and toxins in the blood. Hepatic cells contain enzymes which either break down toxins carried in the blood, transform them into less harmful substances or, failing either of those processes, stores them. For example, metabolism of amino acids will result in the release of free amino acids and nitrogenous wastes, the latter of which are converted by hepatic cells to urea. In moderate amounts, this urea is harmless and is easily excreted by the kidneys and sweat glands. "Old" red blood cells and certain bacterial can also be destroyed and, in the case of the former, recycled by the Kupffer cells.

In short, the liver is vital to maintaining the body's normal biochemical state. Impairment or loss of its function can, therefore, be fatal. A concise summary of known possible derangements of hepatic metabolism can be found in Podolsky, et al., "*Derangements of Hepatic Metabolism*" Ch. 315, *Principles of Internal Medicine*, 10th ed., pp. 1773–1779, 1983. The medical art has developed several approaches to the treatment of, or compensation for, liver disease, damage and failure. In addition, humans (as well as many other species) are capable of regenerating lost or damaged liver tissue.

However, although supportive and pharmaceutical treatments or transplantation may alleviate or reverse many symptoms of liver disease, these methods all require time which an actually ill patient may not have. Further, while undergoing treatment, support for any loss of normal liver function must be provided to maintain or approximate metabolic homeostasis. A means, therefore, is needed which can perform the cleaning functions of the liver when it cannot, thus increasing the time available for treatment.

Extracorporeal liver perfusion (i.e., pumping blood through foreign liver tissue) has been a proposed means for treatment and support for many years, with mixed success. An example of the use of repeated liver perfusions for long-term hepatic support can be found in Abouna, et al., "*Long-Term Hepatic Support by Intermittent Liver Perfusions*", *The Lancet*, pp. 391–396, (Aug. 22, 1970), which reports maintenance of a patient suffering from liver failure for 76 days using periodic liver perfusions. However, despite attempts to use liver tissue from 5 different species, immunological and other biochemical reactions limited the use of the perfusions and the patient died before a suitable transplant donor could be found.

Isolated hepatocyte transplantation has also be performed, again with mixed results (see, e.g., Makawo, L., et al., *Can. J. Surg.*, 24:39–44, 1981, and Demetriou, et al., *Proc. Natl. Acad. Sci. USA*, 83:7475–7479, 1986).

In contrast, extracorporeal methods of purifying blood and plasma; i.e., by hemodialysis, hemoperfusion or hemofiltration are well-known and established in the art for treatment of renal insufficiencies. The major goal of these methods is to maintain fluid and electrolyte balance and rid the body of waste products.

In renal hemodialysis, blood is pumped into a dialyzer containing an artificial semipermeable membrane suspended in a dialysis solution. With a concentration gradient established across the membrane for a particular substance, flow from the blood into the dialysis bath will occur. This method can be used to successfully lower the concentration in blood of urea and in plasma of potassium. Net removal of substances whose concentrations should not be altered in blood or plasma, such as sodium in the latter, can be removed by establishing a hydrostatic pressure gradient across the membrane, creating a convective pathway for movement of solutes across the membrane. Details concerning the structure of a conventional hemodialysis device as well as means for controlling fluid temperature, dialyzate concentration, and fluid flow therein are set forth in several existing patents, including, respectively, U.S. Pat. No. 5,011,607 to Shinzato, U.S. Pat. No. 4,923,598 to Schal, U.S. Pat. No. 4,894,164 to polaschegg, and U.S. Pat. No. 5,091,094 to Veech.

In operation, blood is removed or pumped directly from the patient into the dialyzer and flows along one side of the membrane. The dialysis solution is pumped in counterflow across the membrane; effluent blood is returned to the patient.

Hemodialysis according to the method outlined above is most effective for the removal of small molecular weight species that are water-soluble and not protein-bound. As a result, it is principally used in therapy for renal insufficiencies, although it may be used in the treatment of certain drug overdoses. To use the method effectively to compensate for loss of liver function, however, additional strategies for blood detoxification are required.

To that end, a number of implantable and extracorporeal bioartificial liver devices have been proposed in the art and tested in clinical trials (see, e.g., the review in Nyberg, et al., Am.J.Surg., 166:512–521, 1993). Although the design and operation of such devices have varied widely, they share common elements. For example, the devices typically utilize isolated hepatocytes to metabolize solutes from blood which pass through as well as one or more permeable membranes. Of the devices which utilize isolated hepatocytes, the hepatocytes are typically anchored onto a supporting substrate to facilitate cellular differentiation and aggregation.

For example, using many of the concepts disclosed in the parent application of this continuation-in-part application, a bioartificial liver containing hepatocytes bound to collagen-coated microcarrier beads (CYTODEX 3 beads, a trademarked product of Pharmacia) in a hollow fiber containing bioreactor was tested and described as producing more efficient metabolite transfer than systems which entrap hepatocytes within gel or gel droplets (Rozga, et al., *Biotech. and Bioengineering*, 43:645–653, 1994; see also, Miura, et al., *Artif.Org.*, 10:460–465, 1986 [re use of a calcium alginate gel as a cell support], and Cai, et al., *Artif.Org.*, 12:383–393, 1988 [microencapsulation of cells in a gel]).

Other approaches to the use of isolated hepatocytes in an artificial liver have attached the cells to microcarriers and placed them into a chromatography column for perfusion (Demetrious, et al., *Ann.Surg.*, 259–271, 1986), onto hollow fibers (Jauregui, et al., *J.Cell Biochem.*, 45:359–365, 1991; see also, U.S. Pat. No. 5,043,260), onto glass plates stacked in a module and perfused with oxygenated medium (Uchino, et al., *ASAIO Proc.*, 34:972–977, 1988), onto asialoglycoprotein polymers (Akaike, et al., *Gastroenterol.*, 28 Supp. 45–52, 1993), and into beds packed with matrix-forming materials such as glass beads (Li, et al., *In Vitro Cell Dev. Bio.*, 29A:249–254, 1993). The efficacy of these approaches has been limited by relatively short periods of cell viability (as short as a few hours; Demetriou, et al.), difficulties in forming cell aggregates, and diminished contact between the cells and nutrients, metabolites and toxins (as a result of immobilization of the cells onto a substrate which masks a portion of the cell surface).

Over time, techniques to improve cell viability and aggregation have been improved (see, e.g., published patent application 93-272876 [WO 9316171], which describes a system similar to that disclosed in Li, et al., *In Vitro Cell Dev. Bio.*, supra). However, it has been generally accepted in the art that hepatocyte aggregation and function sufficient for use in extracorporeal liver support are dependent at least on attachment of the cells to a substrate or matrix, if not also immobilization of the cells (see, e.g., Rotem, et al., *Biotech. and Bioengineering*, 43:654–660, 1994 [hepatocytes are anchorage dependent cells]; Miura, et al., *Biomatter Artif. Cells Artif. Org.*, 18:549–554, 1990 [hepatocyte aggregation is required for proper cell function; to that end, immobilization of the cells is preferred]; Rozga, et al., *Ann. Surg.*, 217:502–511, 1993 [attachment of cells to microcarriers enhances cell function and differentiation]; and, Rozga, et al., *Biotech. and Bioengineering*, supra [attachment of cells to microcarriers or entrapment of cells in a gel preferred]). In contrast, conventional hemodialysis utilizing a membrane against a suspension of free (i.e., "unattached"), isolated hepatocytes has not been shown to be clinically effective in providing liver support (see, e.g., Olumide, et al., *Surgery*, 82:599–606, 1977). Thus, the bioartificial liver devices that utilize isolated hepatocytes which are presently being developed and tested in the art anchor the cells to a substrate, a process which entails a relatively delicate manufacturing step informing the cell/substrate attachment, and risks damage to the cells.

SUMMARY OF THE INVENTION

The invention consists of an device and method for using it to purify (i.e., detoxify) a biological fluid such as blood or plasma, whereby blood or separated plasma is circulated through a bioreactor having at least one semi-permeable membrane passing therethrough. The semipermeable membranes may be in tube, film or hollow fiber form (preferably the latter), and are surrounded by a sterile cell culture medium in solution for maintenance of hepatocytes and/or a hepatoma cell line (as explained further below, the term "hepatocyte" will, unless context otherwise requires, refer both to isolated hepatic cells and a combination of those cells which Kupffer bile duct epithelial and endothelial cells and, in some instances, fibroblasts). Soluble proteins, glucose and toxins in the blood or plasma diffuse across the membrane into the culture medium for metabolism by the hepatocytes.

In one embodiment, the hepatocytes utilized in the invention are attached to biologically compatible microcarrier particles. Circulation of the microcarriers in the cell culture medium is assisted by means such as an alternating magnetic field to affect magnate embedded within the microcarriers. As the diffused molecules (i.e., solutes) come into contact with the bound hepatocytes they are taken up by the cells and broken down, transformed or stored according to normal hepatic cell function with respect to said molecules. Effluent blood or plasma (after recombination with a previously separated fraction of red blood cells) is then returned to the patient.

In the preferred embodiment of the invention, unattached hepatocytes (i.e., cells which are not attached to a substrate or otherwise immobilized) are utilized. Means are provided to facilitate cell aggregation within the device (i.e., in situ) to provide extracorporeal liver support to a patient in need of such support.

Additional purification means such as a hemofiltration device, means for adsorption onto an activated charcoal column or other resin adsorbents and/or a conventional dialysis device may also be provided as needed to remove certain toxic drug or waste products not broken down or stored by the hepatocytes (such as urea excreted thereby into the culture medium). Means may also be provided in the device to remove any antibodies formed to the hepatocytes or, for example, to xenogeneic grafts of liver tissue in transplant patents not captured by the hepatocytes.

BRIEF DESCRIPTION OF THE DRAWINGS

FIG. 2 is a schematic representation of an alternative embodiment of the device of the invention, including preferred additional purification means.

DESCRIPTION OF THE PREFERRED EMBODIMENTS

A. Isolation an Preparation of Cells

Figure 1:
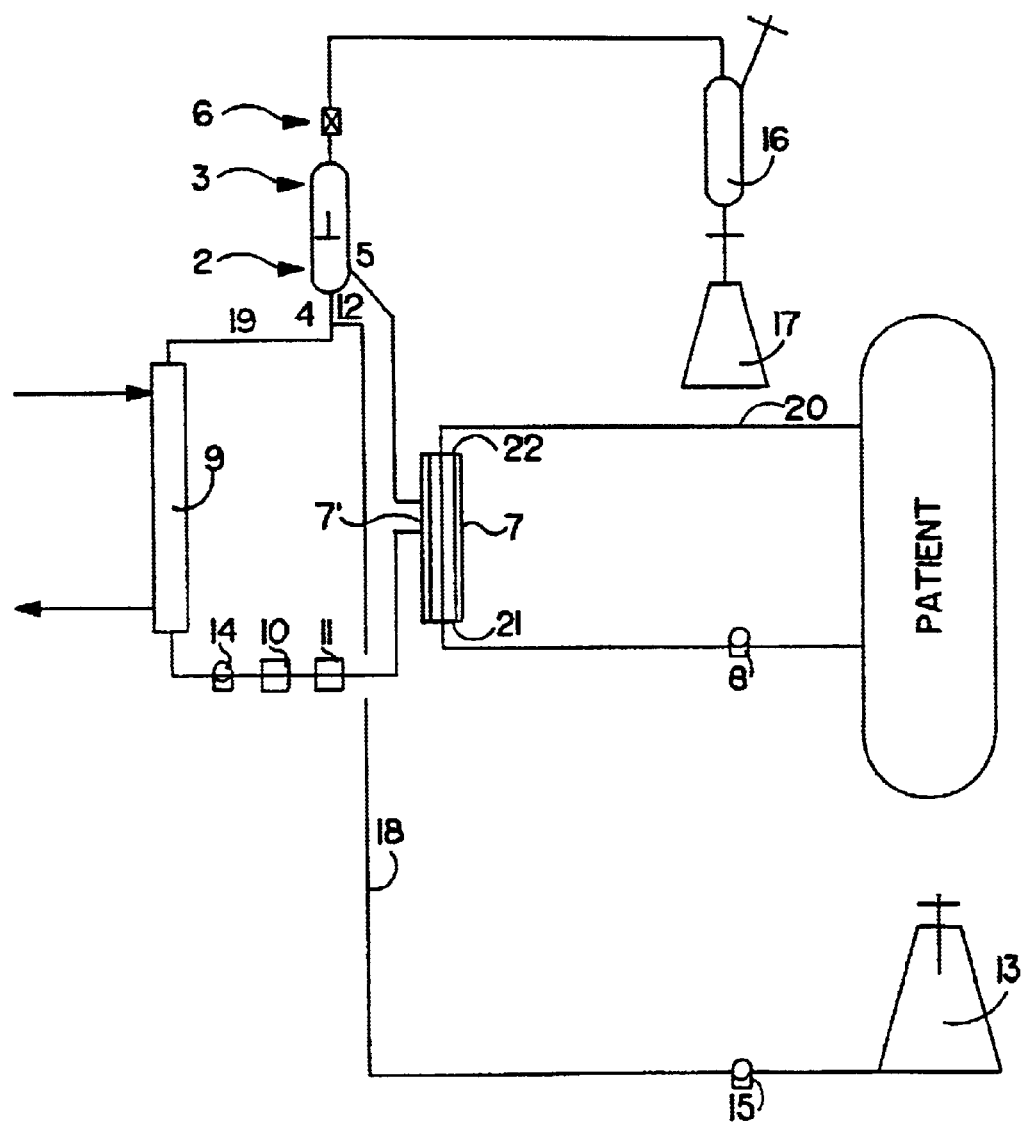
FIG. 1 is a schematic representation of a preferred embodiment of the device of FIG. 1 for use with unattached hepatocytes.

A principal feature of the invention is its use of living, isolated liver cells to assist in the purification of substances out of blood or plasma which would, absent liver diseases, impairment or failure, be removed by the patient's own liver. For most embodiments, the cells will be hepatocytes of nonhuman, human, or xenogeneic origin. However, it will be understood by those of skill in the art that hepatoma cells may also be used as the liver cells of the invention. Thus, while hepatocytes are the preferred liver cells due to the lesser risk of pathogenesis that they pose, the word "hepatocyte" and the disclosure herein will be understood to encompass hepatoma cells, such as the human hepatoma cell line Accession No. CRL 8024, which is available from the American Type Culture Collection, Rockville, Md.

Preparation of hepatocytes for use in the invention is as follows:

Methods for isolation of human hepatocytes suitable for use in the method of the invention are known in the art (see, e.g., Takahashi, et al., *Artif. Org.*, 17:653–659, 1993). The use of human hepatocytes in an artificial liver system may reduce the risk of immunologic reaction by the patient to contact with nonhuman hepatocytes. However, the availability of human hepatocytes is necessarily limited. Therefore, of nonhuman hepatocytes, porcine hepatocytes are preferred for use in the invention principally because of their availability and physiologic similarity to human hepatocytes. It is also anticipated that, for use of the system with liver transplant patients, porcine hepatocytes will be particularly useful where porcine tissue can be modified to be a xenogeneic organ source for human transplantation. It will be appreciated by those skilled in the art, however, that other mammalian species may also be suitable sources for the hepatocytes of this invention.

Using porcine tissue as an example, therefore, hepatocytes in lobules are retrieved from the liver immediately following slaughter of the animal. The lobular tissue is screened for disease according to means known in the art. Hepatocytes are then isolated from the lobular tissue by enzymatic (collagenase) digestion according to means known in the art and purified (see, e.g., techniques described in Berry, et al., *J. Cell. Biol.* 43:506–520, 1969; Seglen, *Methods Cell Biol.* 13:29–83, 1976; and Example I, infra). Depending on the method of isolation used, Kupffer cells and other cellular components of the lobular tissue (such as bile duct epithelial cells) may also be included with the hepatocytes. If desired, the hepatocytes may be further purified by pelleting the cells at low speed (e.g., 50 Xg), in a reagent such as the 60% PERCOLL solution supplied commercially by Sigma Chemical of St. Louis, Mo.

Because the biochemical states which contribute to or cause liver disease are not completely understood, it is not yet known the extent to which each of these cell populations may contribute or be necessary to the function of the invention. It is expected that the use of purified populations of hepatocytes will be preferred; however, as used herein, the term "hepatocyte" should be understood to encompass hepatic cells or fibroblasts alone or in combination with Kupffer cells, bile duct epithelial and endothelial cells. It may also be desirable to utilize cells which have bene genetically altered to produce or metabolize liver specific products such as albumin or clotting factors. These cells could be used exclusively or in a cocktail with native hepatocytes.

Once purified, one or more hepatocytes may be attached for use in one embodiment of the invention to a biologically inert carrier, preferably beads of 150–200 $\mu$m in diameter. Preferred for use in this regard are natural polymer materials such as dextran beads, available under the trade name CYTODEX 3 by Pharmacia LKB Biotechnology of Uppsala, Sweden. Equivalent materials such as agarose beads (available from Bio-Rad, Inc. of Richmond, Calif.) or other substrates such as glass may also be used. Therefore, although for convenience the substrate to be used to support the hepatocytes in the invention will be referred to as beads, those of skill in the art will know of, or can readily ascertain, other support substrates suitable for use in this embodiment of the invention.

The beads will preferably be coated with denatured collagen or equivalent biological material to permit attachment of the hepatocytes thereto. Collagen is the preferred surface because exogenous fibronection is not required for attachment of hepatocytes to collagen.

Examples of suitable methods can be found in "*Microcarrier Cell Culture: Principles and Methods*" available on request from Pharmacia LKB Biotechnology, in Gjessing, et al., *Exp. Cell. Res.* 129:239–249, 1980, and in Demetriou, et al., *Science*, 23:1190–1192, 1986, the disclosures of which are incorporated herein by this reference to illustrate knowledge in the art concerning cell attachment to microcarrier substrates. For example, using a commercially available spinner vessel, 10 mg. of dextran beads can be added to each milliliter of cell culture. Hepatocytes, to a final concentration in the cell culture medium of $1 \times 10^3$ cells/ml., are added to the beads, mixed gently and incubated at 37° C. Periodic stirring may be necessary as the cell culture medium volume is increased if attachment is not achieved readily.

However, in the preferred embodiment of the invention, the hepatocytes will not be attached to a substrate or otherwise immobilized. Therefore, for use in this embodiment of the invention, hepatocytes will be isolated as described above and will be stored as described below.

The attached or unattached hepatocytes may be preserved by maintaining them at a temperature of less than −75° C. in a sterile environment. Preferably, they will be frozen and stored in a container of liquid nitrogen and maintained according to substantially the same method used to preserve isolated spermatocytes for artificial insemination. A particularly suitable method for cryopreservation of hepatocytes is described in Rozga, et al. *Biotech. and Bioengineering*, 43:645–653, 1994. An alternative method for cryopreserving hepatocytes is described in Dixit, et al., *Transplantation*, 55:616–662, 1994, wherein cells are encapsulated and frozen in calcium alginate. By freezing the hepatocytes, it may be possible to store the cells for periods of several years, although storage for periods of less than a year would be preferred. However, most preferably, to the extent practical, the hepatocytes will be used shortly after isolation.

For use of the hepatocytes, the cells will be suspended in a biocompatible culture medium. If frozen, the cells may be thawed and washed in a suitable buffer, such as phosphate buffered saline. Preferably, the culture medium will contain nutrients and other supplements to maintain the viability of the hepatocytes, which nutrients and supplements are known to, or may be readily ascertained by, those of ordinary skill in the art. An example of a culture medium suitable for use in hepatocyte maintenance is the medium sold under the trade name RPMI-1640 by Grand Island Biologicals, Grand Island, N.Y. Another suitable and commonly used culture medium is the WAYMUTH medium supplied commercially by GIBCO Laboratories, Grand Island, N.Y. Preferably, the medium will be supplemented with salts or nutrients known to those skilled in the art depending on the needs of the particular cells used in the system (i.e., which may vary depending on whether cells other than hepatocytes are included, the length of use of the hepatocytes, the specific substances to be metabolized, etc.). Such additives may include one or more amino acids, nutrients and stabilizers such a salanine, serine, asparagine, albumin, aminoleulinic acid, oleci acid, dexamethasone, thyroxine, tocopherol, glucagon, insulin and gentamicin, all of which are commercially available. A suitable supplemented culture medium is described in detail in Example I, infra. Alternatively, particularly if the hepatocytes are to be used for purification purposes within about 6 hours of isolation or thawing, the culture medium may be any blood compatible fluid, such as saline.

B. Bioartificial Liver Devices Suitable for Use in the Methods of the Invention 1. Construction and Operation of a Device Preferred for Use With Unattached Hepatocytes Referring now to the drawings, FIG. 1 depicts a preferred embodiment of the device of the invention for use primarily with unattached hepatocytes, while FIG. 2 depicts suitable modifications of the device of FIG. 1. The devices of the invention are generally are composed of a purification bioreactor having at least one semipermeable membrane therethrough, and at least two pumps or other means for circulation of the hepatocytes and blood or plasma through the device. Generally, each device encompassed by the invention will include a first conduit (i.e., biological fluid loop 20) and a second conduit (i.e., hepatocyte loop 5), which conduits are separated by at least one semi-permeable membrane. All of the components of the device (including connectors, clamps, leur-locks, tubing, and containers) will preferably be sterilizable.

In addition, means for sensing and controlling flow temperature and pressure of the dialyzate and blood, as well as determining the relative concentration of solutes therein, are known in the art and, where noted below, may be suitable for use in the device of this invention. For purposed of illustration, reference may be made for these details to the references identified in the background section, supra.

Fluids in biological fluid loop 20 will enter it substantially at body temperature and should be returned to the patient at substantially the same temperature. Maintenance of this field temperature will be achieved by external temperature control means for blood and plasma known to those skilled in the art; e.g., means used to maintain the temperature of fluids during plasmapheresis, blood bank storage or transfusion. Means for temperature control of fluid during renal hemodialysis and/or hemofiltration are also described in U.S. Pat. No. 4,894,164 (disclosing a technique for cooling blood exposed to heated dialyzate during renal hemodialysis). A proposal for maintaining the blood temperature at 34° C. could also be utilized with the process of this invention (see, e.g., Maggiore, et al. *Proc. EDTA* 18:597–602, 1981). An oxygen source (i.e., oxygenator 9) will also be provided to supply oxygen to the hepatocytes.

One particularly suitable means for temperature control places most of the components of the device within an insulated incubator sufficient to maintain the temperature of the fluids circulating within the device at about body temperature (e.g., 37° C. for humans). Suitable incubator materials will be known to, or can be readily ascertained by those of skill in the art and include foam or glass in a durable container, such as stainless steel.

It should be noted that operation of the entire system, including control of the valve means and the initiation and cessation of flow into and out of mixing vessel 1 and stations within the hepatocyte loop 5, as well as flow into, through and out of the biological fluid loop 20, will preferably be substantially continuous within a purification cycle. Control of the system will preferably be by control means (not shown) such as a microprocessor with manual override capabilities according to means well-known in the art and used in the control of devices for renal hemodialysis and hemofiltration.

Alternatively or preferably in addition to these electronic control means, manual control means (not shown) will be provided throughout the system to allow a skilled operator to open and close the flow valves into and out of each station within biological fluid loop 20, control the pump means 8, 14 and 15, and control flow into and out of hepatocyte loop 5.

In addition, although pump means are depicted in FIG. 1 at particular locations, it will be appreciated by those skilled in the art of mechanical engineering that one or more of such pump means may be included in the loops at sites other than the ones shown.

Referring to FIG. 1, a preferred embodiment of the device includes a mixing vessel 1 into which unattached and uncontaminated (i.e., "new") hepatocytes will be introduced and circulated to facilitate their aggregation prior to introduction of the cells into the purification bioreactor 7 via hepatocyte loop 5. The mixing vessel 1 will include a hepatocyte introduction port 2 (for introduction port 3 (for the removal of contaminated (i.e., "old"), hepatocytes and culture medium from mixing vessel 1), hepatocyte circulation outlet port 4, hepatocyte circulation inlet port 5 and a waste outlet 6. Conveniently, these ports may be formed of tubing attached to and through a wall of mixing vessel 1.

For example, where mixing vessel 1 is formed of glass, ports 2–6 may be formed of glass tubes fused into and through the wall of vessel 1 at suitable locations, such as those shown in FIG. 1. The ports may also be attached to mixing vessel 1 with a luer-lock or equivalent fitting attached to the port via flexible tubing that can be cloned using a hose clamp or similar clamping means. Other designs and materials for ports 2–6 will be apparent to those of ordinary skill in the art and will not, therefore, be described in detail here.

The hepatocyte loop itself (exclusive of stations identified infra) will be a conduit formed of arterial flexible tubing or biologically compatible materials similar or identical to those used to form mixing vessel 1 and purification bioreactor 7. Hepatocyte loop 5 will be sealably attached to mixing vessel 1 at outlet port 4 and inlet port 5. Conveniently, the seal attachment may be made by an O-ring and O-ring joint clamp, the latter of which will allow adjustments to be made to increase or decrease the tension on the O-ring seal.

The mixing vessel 1 and purification bioreactor 7 must be of a biologically compatible, non-cytotoxic material and will be preferably be of a polymer compound such as acrylonitrile butadiene styrene ("ABS") resin plastic, polypropylene, polysulfone, glass or equivalent materials composed to meet USP XXI Class VI toxicity testing standards.

The size of mixing vessel 1 may vary, but will generally be sufficient to retain a number of hepatocytes equivalent to at least 1% of the approximate weight of the liver in the mammalian species to be treated; i.e., a "theoretical minimum" number of cells. For example, in humans, the theoretical minimum number of cells which would be expected to be effective in extracorporeal purification of blood or plasma is about 1% of the liver's hepatocytes or about 2 billions cells. The mixing vessel will, therefore, be sufficient in size to contain at least a theoretical minimum number of hepatocytes suspended in a sterile, biologically compatible fluid such that the hepatocytes may be circulated within mixing vessel 1; i.e., the cells will not be packed to the point of immobilization within the mixing vessel.

The size of the purification bioreactor 7 will depend on the volume of blood or plasma to be circulated through the system. It is expected that this volume will vary from ½ pint to 4 pints, with the former being the volume expected to be circulated in a pediatric application and the latter being the upper limit expected to be available for adult applications with use of plasma expanders and plasma blood products.

Purification bioreactor 7 is in fluid communication with a source of biological fluid (e.g., blood or plasma) to be treated by external connection which form a circulation loop for the biological fluid (e.g., blood or plasma) to be treated. The purification bioreactor will preferably be a hollow fiber bioreactor. In a hollow fiber bioreactor, the circulation of biological fluid through purification bioreactor 7 will occur through a multiplicity of capillaries (representatively depicted as 7' in FIG. 1) formed of semipermeable membranes which will allow the exchange therethrough of soluble proteins (which may include antibodies) and metabolic waste products of sizes which will vary according to the application.

To this end, the membrane pore size is expected to vary upward to a pore large enough to permit passage of proteins therethrough, with the larger pore size intended for removal of proteins such as antibodies. It should be noted that where larger pore sizes are used, certain desirable substances (e.g., plasma proteins) may diffuse into the culture medium. Means for return of these substances are provided below; because of this phenomenon, however, it is expected that pore sizes of about 0.2 $\mu$m in diameter will be most practical and will result in significant fluid convection, which is the primary force responsible for solute transport across the membranes that form the hollow fibers.

A commercially available and suitable product for use as purification bioreactor 7 is the ZYMAX hollow first bioreactor (ZYMAX is a registered trademark of Microgeon, Inc. of Laguan Hills, Calif.) The ZYMAX product comprises a collection of 3600 hollow fibers formed of a semipermeable membrane material having a pore size of 0.2 $\mu$m formed of mixed esters of cellulose which allows free passage of soluble proteins and metabolic wastes therethrough. The fibers are contained within a ported, biologically compatible and non-cytotoxic polysulfone housing; fittings, including clamps, gaskets, hoses and plugs necessary to construct the bioreactor from the manufacturer. Other suitable hollow fiber bioreactors are the Z22M-060-01X bioreactor from Microgon (which has only 670 fibers, but uses fibers or longer length [about 550 as potted end] than may conventional bioreactors), and [OTHER EXAMPLES????????]

The total number of hollow fibers (shown as 7' in FIG. 1) required to dependent on the volume of culture medium contained within purification bioreactors 7, which is in turn dependent on the volume of biological fluid to be purified within the invention system (which will determine the number of hepatocytes to be suspended within the culture medium). For example, given a known volume of blood or plasma and the volume and permeability of the hollow fibers (approximately 2300 milliliters in the lumens and 0.2 $\mu$m respectively for a single ZYMNAX bioreactor), the total number of fibers and volume of culture medium can be estimated. As a general principle, the total respect to the volume of culture medium to ensure contacting of solutes from the blood and plasma with hepatocytes circulating through purification bioreactor 7 in hepatocyte loop 5.

Within purification bioreactor 7, hepatocyte loop 5 comprises the extracapillary space within the bioreactor housing, while biological fluid loop 20 comprises the intracapillary space; i.e., the lumens of the hollow fiber 7' contained with bioreactor 7. The movement of hepatocytes through the hepatocyte loop is driven by pump 14 (e.g., a peristaltic pump), while the movement of blood or plasma through the biological fluid loop is driven by pump 8 (e.g., a blood monitor pump).

As indicated in the background discussion preceding this disclosure, it is highly desirable that the hepatocytes in an artificial liver system aggregate together. For example, it has been previously shown that unaggregates, single hepatocytes in culture relatively rapidly compared to cells in aggregates. For that reason, prior art artificial liver systems provide an extracellular solid substrate to allow the hepatocytes to aggregate within a bioreactor and/or culture the cells in a manner which encourages the formation of aggregate spheroids before use of the cells in an artificial liver system.

The process by which hepatocytes aggregate requires energy. Thus, although not absolutely necessary to their survival, the viability of hepatocytes for use in an artificial liver system has been shown to be enhanced by the presence of oxygen, particularly in the early stages of aggregation (see, e.g., Rotem, et al., *Biotech. & Bioengineering*, 43:654–660, 1994 [oxygen partial pressure of about 0.064 mmHg required for half-maximal attachment of a single layer of hepatocytes to a collagen-based substrate, while about 0.13 mmHg was shown to be required for the cells to spread across the substrate]). Where hepatocytes is an artificial liver system or culture are present in multiple layers, it has been suggested that oxygenation of the cells beneath the surface of the top layer may require shortening the diffusion distance between hepatocytes and the oxygen source or increasing the concentration of oxygen present in the early stages of aggregation (Rotem, et al., supra at 659).

In the preferred embodiment of the invention, the hepatocytes are neither immobilized onto a solid substrate nor precultured into aggregate spheroids. Instead, the cells are introduced directly into a circulation suspension of blood compatible fluid (preferably saline or a hepatocyte culture medium as described supra) and encouraged to aggregate in situ. This utilization of the hepatocytes of the invention eliminates the work involved in preculturing the cells, eliminates the work involved in attaching the cells to a solid substrate, ensures that the entire surface of each cell is available for interaction with other cells, oxygen, nutrients and metabolites in the culture medium, minimizes the potential damage to each cell inherent in the handling involved in preculturing the or immobilizing the cells, and shortens the time between isolation and use of cells in the method of the invention.

To ensure adequate oxygenation of unattached hepatocytes in the circulation suspension, mixing vessel 1 is filled with a blood compatible fluid which is driven by pump 15 from a feed reservoir 13 or other fluid source through line 18. The fluid is oxygenated by oxygenator 9, which may be any conventional fluid oxygenator known in the art. For oxygenation, recycle pump 14 is activated such that the fluid in line 18 passes into line 19 through a valved feed line 12 at outlet port 4 and through oxygenator 9. Leaving oxygenator 9, the culture medium passes pH probe 10 and dissolved oxygen probe 11.

The pH and oxygen probes will be set at desired set points and the gas composition of the culture medium adjusted accordingly. The culture medium will be maintained at a pH of about 7–8, preferably about 7–7.5, and most preferably about 7.35. The oxygen composition of the culture medium will be maintained between about 0 and 20%, preferably not lower than about 5%. Most preferably, the oxygen composition will be about that of saturated air at the time that the hepatocytes are introduced into the culture medium. The oxygen composition is adjusted by increasing or decreasing the concentration of oxygen introduced into the culture medium in oxygenator 9, while the pH of the culture medium may be controlled by increasing or decreasing the concentration of carbon dioxide introduced into the culture medium at oxygenator 9, as appropriate. The balance of the gaseous passes ill be nitrogen. Gas is introduced into the culture medium in the oxygenator in a direction of flow opposite the direction of flow of the circulation fluid. As the culture medium enters mixing vessel 1 through outlet port 4, gas leaves the system through waste outlet port 6 into degassing vessel 16.

Flow through the biological fluid loop will be as follows. Blood or plasma for purification will be either removed from the patient for introduction into the system or, preferably, flow will be generated directly from the patient. In the preferred embodiment, vascular access will be provided according to medically accepted techniques such as those used for acute or chronic renal dialysis (e.g. catheterization, direct anastomosis of native vessels or artificial grafts). In the most preferred embodiment, the biological fluid for purification will be plasma. After removal of blood from the patient, the plasma fraction is separated from the red blood cells by plasmapheresis, using a method and device (not shown) well known in the art. Plasmapheresis may be performed independently and out of the biological fluid loop, but the means therefor will preferably be included in the loop so that direct vascular access to the patient is with the plasmapheresis device.

The plasma fraction (or unseparated blood where plasmapheresis is not performed) passes through biological fluid loop 20 to allow fibers 7' via a connection conduit (not shown) to each fiber or, for the preferred embodiment using a bioreactive housing such as the ZYMAX product, to each such housing wherein said conduits will be provided and attached thereto according to the housing manufacturer's specifications. The structure of the conduits may vary widely according to the number and structure of the hollow fibers 7' used, but will be formed of a biologically compatible, non-cytotoxic material similar to that disclosed above for use to form mixing vessel 1 or an arterial flexible tubing known in the art. Valve means 21 and 22 can be provided at the input and ouptut ports (not shown) of the biological fluid loop 20. Preferably, valve means 21 will be pressure regulated (by, for example, pressure regulator 24 shown in FIG. 2) so effluent blood returned to the patient is at an adequate pressure. Suitable valve means are well known in the art are not, therefore, described further herein.

Flow of blood or plasma through biological fluid loop 20 can be generated by the pressure gradient between the fluid pressure of the blood or plasma as it leaves the patient, but will preferably be assisted by a low pressure mechanical pump means 8 preceding the input portal to biological fluid loop 20, which will preferably be fitted with a pressure regulator (not shown) to prevent any back surge. A suggested placement of flow sensor 25 and control means 30 are schematically depicted in FIG. 2. As suitable means for flow control are well-known in the art, no further description thereof will be provided here. It may also be necessary to provide means for release of air (not shown) from purification bioreactor 7; again, such means are well-known in the art and not described further here.

Noncellular components of blood or plasma introduced into bioreactor 7 via biological fluid loop 20 will exchange across the membrane comprising hollow fibers 7' with the culture medium in the hepatocyte loop. Once the exchange is complete, hepatocytes are introduced into mixing vessel 1 through hepatocyte introduction port 2, then additional culture medium added as needed to ensure that the mixing vessel 1 remains completely filled with fluid. Alternatively, the hepatocytes may be introduced into mixing vessel 1 as the culture medium is being exchanged with the plasma.

In this respect, those of skill in the art will appreciated that the use of unattached hepatocytes requires a delicate balance to be achieved between the flow rate in the hepatocyte loop sufficient to facilitate content between, and aggregation of, the hepatocytes, while causing the cells to shear or otherwise degrade. At the same time, the need to shorten beneficial quantity of blood or plasma must be balanced against the need to optimize the rate of which solute transport across the membranes which comprises hollow fibers 7' into the hepatocyte loop (i.e., into the extracapillary space of bioreactor 7) will occur.

To this end, the direction of flow in the biological fluid loop 20 will be substantially opposite the direction of flow in the hepatocyte loop 5. Through activation of recycle pump 14 in a direction opposite that used to oxygenate the culture medium, the cell-containing circulation fluid in the hepatocyte loop will flow from mixing vessel 1 through bioreactor 7, past probes 10 and 11 and through oxygenator 9 at a rate of about 20 to 80 milliliters of fluid/minute, preferably at a rate of about 65 milliliters of fluid/minute. At the same time, through activation of blood monitor pump 8, blood or plasma in the biological fluid loop will be maintained at a rate of about 20 to 250 milliliters fluid/minute, with a rate of 150–200 milliliters fluid/minute being preferred.

It should be noted that the flow rate in the biological fluid loop which may be effectively and simply controlled through the use of a fluid reservoir. By retaining blood or plasma in this reservoir, a store of fluid is available for processing according to the method of this invention at a substantially higher flow rate and volume than would be possible if flow was directly and entirely from the patient. Using the reservoir, therefore, fluid would be collected from the patient, directed to the reservoir, than removed through valve means and pumped through the biological fluid loop as otherwise described herein.

Returning to the passage of flow through biological fluid loop 20, as blood or plasma passes through hollow fibers 7', soluble proteins and metabolic waste products will pass therethrough into the culture medium by virtue of the osmotic pressure gradient between the fluid in the lumens of the hollow fibers and the culture medium in bioreactor 7, as well as the so-called transmembrane pressure.

It will be appreciated that, unlike the process of renal dialysis, no counterflow across hollow fibers 7' is normally provided or desired in this device. Although it can be expected that there may be some back diffusion of solutes which reach a concentration equilibrium vis-a-vis the fluid in loop 20 and the culture medium, such diffusion is preferably avoided by replenishment of the culture medium, compensated by additional purification means (e.g., those shown as 40 and 50 in FIG. 2), as well as minimized by the concentration gradient across hollow fibers 7'.

Counterflow may be important, however, where the pore size of the membrane is required to be large; e.g. when diffusion of larger molecular weight species out of blood is sought. With those species, however, may for example diffuse plasma proteins which should be returned to the patient. In such an application, a multiplicity of channels may be used to capture plasma proteins and return them to the biological fluid loop utilizing a counterflow (see, e.g., the counterflow pump means described in U.S. Pat. No. 5,011,607). For example, if the filtrate to be removed were known to be a certain diameter, smaller plasma proteins (e.g., albumin) could be captured by a second and smaller semipermeable membrane bounded oppositely by a channel (not shown) leading back to biological fluid loop 20. The remaining filtrate, being too large to diffuse across the second membrane, would remain in solution in the culture medium for metabolism by the hepatocytes.

Alternatively, in absence of means to return desirable solutes to the patient, such solutes, in particular plasma proteins, may be independently returned to the patient via known medical practices. This is not, however, a preferred approach because of the risk of infection from foreign blood products.

As a general principle, proteins and waste products (hereafter "solutes") in solution in the culture medium susceptible to being metabolized or stored by the hepatocytes will be absorbed by those hepatocytes which they contact. However, it is expected that the degree of absorption achieved will be limited in at least two respects.

First, certain solutes will remain in solution because they do not contact a hepatocyte, or do not contact a viable hepatocyte; i.e., one capable of absorption of filtrate. It is this latter possibility that gives rise to the second limitation; i.e., hepatocytes may die, become damaged or otherwise be rendered incapable of performing their expected functions in the system.

As it would not be possible to determine or predict when function may be lost to a given hepatocyte, it may be necessary to replace all or a percentage of the hepatocytes used in the invention through sampling port 3. However, as used in the device and according to the method described above, the hepatocyte circulating in the device should remain viable for at least about 6 hours, the period of time which would be expected to be expanded in a single purification treatment of an adult human.

Further, because solutes not absorbed by hepatocytes (due to the factors discussed above or, as would be true of certain toxins, because the solutes are not susceptible to being metabolized by the liver) will remain in the culture medium, additional removal means may be required and periodic replacement of the culture medium will be necessary.

To that end, hepatocyte loop 5 may include a replenishment station (not shown) at sampling port 3 wherein flow through the loop will be temporarily interrupted for removal from and replacement of hepatocytes and, if necessary, culture medium in the system. The replenishment station could comprise a variety of structures, including a sterile and ported tank or conduits having valve means (not shown) from which "used" cells and medium would flow and into which "new" cells and medium would be introduced.

Preferably, this removal and reintroduction would occur at predetermined intervals throughout a purification cycle to ensure optical performance of the process. Because it would be somewhat impractical to recycle all of the hepatocytes and culture medium during a single purification cycle, removal and replacement of a statistical percentage thereof is preferred. This percentage, as well as the intervals at which it will be removed and replaced, will vary according to the volume of medium, cells and biological fluid in the system and, once these values are known, can be determined according to accepted statistical calculations known in the art. Alternatively, or in conjunction with the above method, the entire volume of cells and medium could be replaced after each cycle.

On completion of a purification cycle, blood is returned to the patient or plasma returned first to the plasmapheresis device for recombination with the patient's red blood cells, then returned to the patient via conduits identical to those described above for introduction of blood or plasma into biological fluid loop 20. It will be appreciated that an immunoassay for IgM and/or known liver function tests may be performed to assist in verification of proper and effective performance of the inventive process prior to or after return of the blood to the patient. Depending on the course of treatment indicated and length of cycle required, the purification cycle could be repeated up to two or three times in a single day.

With respect to the additional removal means, once flow in biological fluid loop 20 has passed through bioreactor 7, the fluid therein may pass through one or more additional purification means stations before being returned to the patient or, alternatively, before being passed again through bioreactor 7. Alternatively, and depending on the substance to be additionally removed, these means could be included within hepatocyte loop 5. For example, it will be appreciated that for certain metabolic waste products excreted into the culture medium by the hepatocytes; e.g., urea, removal means will be best situated in the hepatocyte loop 5.

As the biochemical states which contribute to or cause liver failure or damage may vary according to clinical cause (e.g., hepatitis, alcohol or toxic contamination, drug overdose) and are not completely known or understood, it is not clear what extracorporeal liver functions will be required for a particular patient. Nor is it clear which of those functions will be completely or competently performed by the hepatocytes, and which may have to be completed or performed by additional means. However, examples of such means are well known in the medical arts, are representatively depicted in FIG. 2 as additional purification means 40 and 50, and may include:

Adsorbent means for removal of solutes such as urea onto an activated charcoal column or, coated charcoal (such as the filter sold under the trade name "GAMBRO") other resin adsorbents (a commercially available adsorber is available as the "DT" machine [detoxifier] from Ash Medical, Inc. West Lafayette, Ind.).

Conventional dialysis means for removal of small molecular weight species that are water soluble and not strongly bound to protein(s).

Immunoreactive procedures to remove natural IgM antibodies present in human serum that can react with porcine xenoantigens. Examples of immunoabsorbent materials include dialysis membranes sold by VWR Scientific under the trademarks SPECTRA/POR 6, SPECTRA/POR 7 and SPECTRA/POR 1. Lectins attached to SEPHAROSE 6 mb beads can also be used to isolate IgM antibodies (these beads are commercially available from Pharmacia LkB). Isolation and purification means may also be used manually or by automation according to techniques well known in the art; an example of such means is the product sold by Pierce, Rockford, Ill., under its trademark IMMUNOPURE (IgM Purification Kit).

Means for hemofiltration (i.e., means where blood is passed through an extracorporeal circuit through a hemofilter by which an ultrafiltrate of uremic toxins is withdrawn and equal quantity of uremic-toxin-free blood is added in proportion the volume of blood via an exchange element).

The presence or absence of such additional purification means in either loop will increase or decrease the time needed to complete a given purification cycle by the time needed to perform each additional purification step. It will be appreciated, however, that these steps may be performed through use of the means described independent of the inventive system.

It should be understood that sound medical practice dictates the bioreactor 7 may, and preferably will, be disposed of and replaced or sterilized following each purification cycle and will not be used with more than one patient. It is expected that, depending on the course of treatment indicated, each purification cycle would last several hours if performed at a constant rate. In addition, it will be appreciated by those of ordinary skill in the art that more than one bioreactor may be utilized in parallel by providing additional conduit, fitting and pump means such as those described supra with respect to the single bioreactor system depicted in FIGS. 1 and 2.

C. Construction and Operation of a Device for Use With Attached Hepatocytes in the Method of the Invention It will be appreciated by those of skill in the art that the device described supra may be used in detoxifying blood or plasma with attached hepatocytes. However, where attached hepatocytes are used, it will not be necessary to insure that the flow rate of fluid in the hepatocyte loop is sufficient to facilitate cell aggregation. Instead, the rate of flow will be such that contact between the attached hepatocytes is minimized to avoid damage thereto. In addition, the attached hepatocytes may be introduced directly into bioreactor 7 via a replenishment station and/or sampling port in the hepatocyte loop. To this end, the device may be simplified as schematically depicted in FIG. 2.

The use of attached hepatocytes in an artificial liver system presents the drawbacks discussed supra, such as decreased surface area for contact between the hepatocytes and solutes to be metabolized. To compensate for the loss of cellular surface area, means are provided in this embodiment of the device to circulate the hepatocytes within the bioreactor.

This circulation must, however, be performed gently to avoid contacting the inner surface of bioreactor 7, thus damaging or destroying the hepatocytes. Because of this concern, mechanical mixing of the culture medium or shaking of bioreactor 7 are possible but not preferred methods of achieving circulation of the hepatocytes within the bioreactor. Instead, a preferred method of circulation is the application of an alternating magnetic field to the bioreactor.

According to this method, a low frequency AC power supply 31 (e.g., 60 cycles/second) and at least one pair of opposing coils 32 electrically connected thereto are used to generate an alternating, low frequency magnetic field. Coils 32 will preferably be situated opposite one another and externally to bioreactor 7; preferably, they will be housed in a nonconductive housing and attached to opposite external walls of the reactor by any suitable attachment means. A very moderate circulating flow within the culture medium will be generated by response of magnets placed within a percentage of the dextran beads or other microcarriers 23 to which the hepatocytes are attached (shown in FIG. 2 as beads 23A having an "X" therethrough representative of the magnetic particles within selected beads; preferably, a magnetic particle will be placed in at least 1 out of approximately 10 beads). Beads having magnetic particles therein are commercially available from Dynal, Inc. of Great Neck, N.Y. and are sold under the trade name DYNABEADS M-450.

Another useful method of achieving circulation while maximizing contact of solutes with the attached hepatocytes is achieved using a boundary layer pump. Most useful with film or sheet (rather than hollow fiber) membrane, a boundary layer creates a stream of culture medium which moves along the face of the membrane and carries attached hepatocytes therewith. Alternatively, and particularly if the use of hollow fiber membranes is desired, hepatocytes and culture medium could be introduced into an axial conduit (not shown) through the inner diameter of fibers of a sufficient diameter to accommodate said conduit and passed therethrough using a pump to generate centripetal force to spiral or circulate the hepatocytes and medium in the conduit.

Boundary layer pump means, and the use thereof to move solid articles, are described in U.S. Pat. No. 4,335,994 to Gurth. Such pump means (not shown) are available from Discfo Corporation in Santee, Calif. and are sold under the trademark DISCFLO PUMP. Instructions for and assistance with the attachment and use of the DISCFLO PUMP are available from Discflo Corporation.

Except for these modifications, the operation and structure of this alternative embodiment of the device of the invention is as disclosed with respect to the preferred embodiment described supra.

Examples regarding the use of the inventive devices and methods are provided below. The examples are intended to illustrate rather than limit the scope of the invention. Standard abbreviations (e.g., "ml" for milliliters, "min" for minute, etc.) are used.

EXAMPLE I

In Vitro Evaluation of the Artificial Liver Device of FIG. 1 Using Unattached Hepatocytes Hepatocytes were isolated from Sprague-Hawley rats and/or farmer's pigs after slaughter using the technique described in Li, et al., [CITE?], 1990. Briefly, the technique was performed using collagenase (0.5% w/v, type 1) perfusion. The isolated cell population was determined to have over 80% viability as assessed by trypan blue exclusion. Following isolation, the hepatocyte were suspended in WAYMUTH 752/L culture medium supplemented with 11.2 mg/l alanine, 12.8 mg/l serine, 24 mg/l asparagine, 0.168 mg/ml aminolevulinic acid, 0.393 mg/l dexamethasone, 0.03 mg/l glucagon, 20 units/; insulin, and 84 mg/l gentamicin.

The mixing vessel, bioreactor and biological fluid loop were filled with culture medium and equilibrated to a 20% oxygen concentration in a total medium volume of about 350 ml. Ammonia in a concentration of about 20 ug/ml was added to the biological fluid loop as a model waste product for metabolism in the artificial liver device. Approximately 200 million viable rat hepatocytes were injected into the mixing vessel, while an equivalent number of porcine hepatocytes were injected into the mixing vessel of a secod device. Circulation of fluid through the hepatocyte and biological fluid loops was begun and maintained at a flow rate of about 65 ml per min in both loops.

The number of rat hepatocytes still viable in the system after 21 hours is graphically depicted in FIG. 3, while the number of porcine hepatocytes still viable after 6 hours (the total test period applied to the porcine cell containing device) is depicted in FIG. 4. Viability was determined by a conventional technique; i.e., trypan blue exclusion staining.

FIGS. 5 and 6 respectively depict the decrease in ammonia concentration obtained in the culture medium in both devices over a period of 6 hours. As shown in the FIGURES, a substantial decrease in ammonia concentration was obtained. It is predictable based on these data and the data reported in Example II, infra, that the ammonia concentration in blood or plasma can be reduced in a human by a factor of about 10%.

EXAMPLE II

In Vivo Evaluation of the Artificial Liver Device of FIG. 1 Using Unattached Hepatocytes The device of FIG. 1 was prepared for use with rat hepatocytes as described in Example I, except that culture medium was not introduced directly into the biological fluid loop. A venous connection between the biological fluid loop of the device and the femoral veins of a young male pig (weight=about 26 kg) was established. Blood flowing form the femoral veins of the pig was perfused through the bioreactor for about 6 hours at a flow rate of about 150 ml/min, with continuous return of blood to the pig.

The vital signs and blood chemistry of the pig were observed throughout the 6 hour perfusion period. Hepatocytes were collected from the mixing vessel through the sampling post periodically and the viability of the cells evaluated by trypan blue exclusion staining.

FIG. 5 depicts the percentage of hepatocytes will viable during the perfusion period at the time points indicated in the FIGURE.

FIG. 6 depicts the decrease in ammonia concentration measured in blood sampled from the biological fluid loop of the device at the time points indicated in the FIGURE. FIG. 7 depicts the increase in urea concentration measured in the same blood samples at the same time points.

As shown in the FIGURES, the observed efficacy of the system and viability of the hepatocytes circulated through the system as used in vivo was comparable to the in vitro efficacy and viability measurements reported in Example II. The pig did not suffer any detrimental health effects attributable to the use of the artificial liver device.

Although preferred embodiments of the inventive device and methods are disclosed herein, it will be appreciated by those skilled in the art that modifications may be made to the embodiments disclosed without departing from the spirit or scope of the invention, which is defined by the claims appended hereto.

What is claimed is:

1. A device for extracorporeal purification of mammalian biological fluid comprising:
   a bioreactor having inlet and outlet ports for, respectively, ingress and egress of biological fluid; inlet and outlet ports for, respectively, ingress and egress of culture medium; and at least one semi-permeable membrane extending therethrough, which membrane defines a first conduit for ingress and egress of biological fluid and a second conduit for ingress and egress of culture medium;
   a mixing vessel in fluid communication with the second conduit, wherein the mixing vessel has an inlet port for introduction of living, unattached hepatocytes into the culture medium;
   a metal containing substrate within the bioreactor for attachment of hepatocytes wherein at least a portion of the hepatocytes are attached to the metal containing substrate wherein the metal is susceptible to magnetic forces;
   a means for generating an alternating magnetic field wherein the field causes the metal containing substrate to be circulated within the bioreactor;
   oxygenation means in gaseous communication with the mixing vessel;
   pump means for circulation of biological fluid through the first conduit of the bioreactor; and,
   pump means for circulation of hepatocytes and culture medium in the mixing vessel and through the second conduit of the bioreactor.

2. The device according to claim 1 further comprising at least a theoretical minimum number of unattached hepatocytes.

3. The device according to claim 1 wherein additional means for removal therefrom of substances selected from the group consisting of antibodies, toxic substances and metabolic waste products are connected to, and in fluid communication with, the mixing vessel.

4. The device according to claim 1 wherein additional means for removal of solutes including antibodies, toxic substances and metabolic waste products, are connected to, and in fluid communication with, the bioreactor.

5. The device according to claim 3 or 4 wherein the additional means comprise one or more means selected from the group consisting of adsorbent means, conventional dialysis means, immunoreactive procedures and hemofiltration.

6. The device according to claim 1 wherein the semi-permeable membrane is a hollow fiber in which the first conduit is the lumen within the fiber and the second conduit is the space outside of the fiber.

7. The device according to claim 1 further comprising a biological fluid loop, wherein the biological fluid loop is composed of material compatible with fluids selected from the group consisting of blood, plasma and plasma containing plasma extenders.

8. The device according to claim 1 wherein the living hepatocytes are isolated from liver tissue of pigs.

9. The device according to claim 1 wherein the living hepatocytes are isolated from liver tissue of humans.

10. The device according to claim 1 wherein the pump means for circulation of biological fluid through the bioreactor includes a boundary layer pump for movement of the biological fluid through the first conduit of the bioreactor.

11. A device according to claim 6 wherein the pump means for circulation of biological fluid through the bioreactor includes at least one conduit situated coaxially through the hollow fiber semi-permeable membrane through which the fluids is circulated by centrifugal force.

12. The device according to claim 1 wherein the semi-permeable membranes include membranes impermeable to plasma proteins to serve as a barrier for diffusion thereof into the cell culture medium.

13. The device according to claim 1 wherein the pump means for circulation of the biological fluid include a pump to generate a counterflow for back diffusion of the plasma proteins into the biological fluid.

14. The device according to claim 1 wherein the semi-permeable membrane is impermeable to proteins.

15. The device according to claim 1 wherein the semi-permeable membrane is at least partially permeable to proteins.

16. A method for extracoporeal purification of a biological fluid, the method comprising:
- introduction of at least a theoretical minimum number of living, unattached hepatocytes into a mixing vessel of a bioreactor, wherein the mixing vessel is filled with culture medium and is free of air;
- incubation of the hepatocytes with a metal containing substrate to allow attachment of at least a portion of the hepatocytes to the metal containing substrate;
- circulation of the metal containing substrate within the mixing vessel by generating an alternating magnetic field within the bioreactor;
- circulation of the biological fluid through the bioreactor; and,
- circulation of the hepatocytes and culture medium in and from the mixing vessel through a bioreactor having at least one semi-permeable membrane passing therethrough, wherein the membrane separates the culture medium from the biological fluid but allows solutes to pass from the biological fluid into the culture medium.

17. The method according to claim 16 wherein the biological fluid is circulated through the bioreactor at a flow rate of about 20 to 250 milliliters/minute.

18. The method according to claim 16 wherein the culture medium containing the hepatocytes is circulated through the bioreactor at a flow rate of about 20 to 80 millimeters/minute.

19. The method according to claim 16 wherein the culture medium containing the hepatocytes and the biological fluid are circulated through the bioreactor for a period of about 6 hours.

20. The method according to claim 16 wherein all or a portion of the hepatocytes and culture medium are replaced at least once during the circulation period.

21. The method according to claim 16 wherein the biological fluid and culture medium are maintained at about the body temperature of the mammal from whom the biological fluid was derived.

22. The method according to claim 16 wherein antibodies, and/or toxic substances are removed from the biological fluid by additional purification means.

23. The method according to claim 16 wherein metabolic waste products are removed from the culture medium by additional purification means.

24. A method according to claim 16 wherein the semi-permeable membrane is impermeable to proteins.

25. A method according to claim 16 wherein the semi-permeable membrane is at least partially permeable to proteins.

26. A device for extracoporeal purification of mammalian biological fluids comprising:
- a bioreactor having and inlet and outlet ports for, respectively, ingress and egress of biological fluid; inlet and outlet ports for, respectively, ingress and egress of culture medium; and at least one semipermeable membrane extending therethrough, which membrane defines a first conduit for ingress or egress of biological fluid and a second conduit for ingress and egress of culture medium;
- a port in fluid communication with the second conduit for introduction of living hepatocytes wherein at least a portion of the hepatocytes are attached to a metal containing substrate into the culture medium;
- a means for generating an alternating magnetic field wherein the field causes the metal containing substrate to be circulated within the bioreactor;
- pump means for circulation of biological fluid through the first conduit of the bioreactor; and
- pump means for circulation of hepatocytes and culture medium into and through the second conduit of the bioreactor wherein at least a portion of the hepatocytes are attached to a metal containing substrates.

27. The device according to claim 26 further comprising at least a theoretical minimum number of attached hepatocytes.

28. The device according to claim 26 further comprising means for generating an alternating magnetic field wherein the field will cause the metal containing substrate to be circulated within the bioreactor.

29. The device according to claim 27 further comprising additional purification means for removal of antibodies and/or toxic substances from the biological fluid.

30. The device according to claim 27 further comprising additional purification means for removal of metabolic waste substances from the culture medium.

31. The device according to claim 27 wherein the living hepatocytes are isolated from liver tissue of pigs.

32. The device according to claim 27 wherein the living hepatocytes are isolated from liver tissue of humans.

33. The device according to claim 27 wherein the pump means for circulation of biological fluid through the bioreactor includes a boundary layer pump for movement of the fluid through the first conduit.

34. The device according to claim 27 wherein the semi-permeable membranes include membranes impermeable to plasma proteins to serve as a barrier for diffusion thereof into the cell culture medium.

35. The device according to claim 27 wherein the pump means for circulation of the biological fluid include a pump to generate a counterflow for back diffusion of the plasma proteins into the biological fluid.

36. The device according to claim 27 wherein the semi-permeable membrane is impermeable to proteins.

37. The device according to claim 27 wherein the semi-permeable membrane is at least partially permeable to proteins.

38. The device according to claim 27 wherein the substrate comprises microcarrier particles.

39. The device according to claim 38 wherein the particles are collagen-coated beads.

40. A method for extracorporeal purification of a biological fluid, the method comprising:
- introduction of at least a theoretical minimum number of living hepatocytes into a first conduit of a bioreactor;
- incubation of the hepatocytes with a metal containing substrate to allow attachment of at least a portion of the hepatocytes to the metal containing substrate;
- circulation of the metal containing substrate within the mixing vessel by generating an alternating magnetic field within the bioreactor;
- circulation of the biological fluid through a second conduit of the bioreactor, wherein the first and second conduits are separated by a semi-permeable membrane; and,
- circulation of the hepatocytes in the first conduit of the bioreactor.

41. The method according to claim 40, wherein at least a portion of the hepatocytes are replaced at least once during the circulation period.

* * * * *